United States Patent
Aase et al.

(10) Patent No.: US 11,931,206 B2
(45) Date of Patent: Mar. 19, 2024

(54) ULTRASOUND IMAGING SYSTEM AND METHOD FOR SAVING A SEQUENCE OF IMAGES AS A CINELOOP

(71) Applicant: GE Precision Healthcare LLC, Wauwatosa, WI (US)

(72) Inventors: Svein Arne Aase, Trondheim (NO); Brian J. Lesniak, Canandaigua, NY (US); Carolina Bonilla Herrando, Barcelona (ES)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 17/864,197

(22) Filed: Jul. 13, 2022

(65) Prior Publication Data
US 2024/0016478 A1    Jan. 18, 2024

(51) Int. Cl.
*A61B 8/00* (2006.01)
*A61B 8/08* (2006.01)

(52) U.S. Cl.
CPC ............. *A61B 8/463* (2013.01); *A61B 8/08* (2013.01); *A61B 8/483* (2013.01)

(58) Field of Classification Search
CPC ............ A61B 8/463; A61B 8/08; A61B 8/483
See application file for complete search history.

(56) References Cited

U.S. PATENT DOCUMENTS

| 6,447,453 B1 | 9/2002 | Roundhill |
| 2021/0369241 A1 | 12/2021 | Aase |

OTHER PUBLICATIONS

Mishra et al., Chapter 3—Generic SoC Architecture Components, System on Chip Interfaces for Low Power Design, Morgan Kaufmann, 2016, pp. 29-51, ISBN 9780128016305, https://doi.org/10.1016/B978-0-12-801630-5.00003-7. (https://www.sciencedirect.com/science/article/pii/B9780128016305000037).*

* cited by examiner

*Primary Examiner* — Bo Joseph Peng

(57) ABSTRACT

An ultrasound imaging system and method of ultrasound imaging. The method includes initiating a live ultrasound scanning session and saving a first sequence of images in a volatile memory. The method includes receiving a store command while in a retrospective image capture mode during the live ultrasound scanning session. The method includes detecting that the first sequence of images does not meet a length threshold and automatically continuing to acquire a second sequence of images. The method includes detecting that the combination of the first sequence of images and the second sequence of images meets or exceeds the length threshold and saving a third sequence of images as a cineloop in a non-volatile memory, the third sequence of images including both at least a portion of the first sequence of images and at least a portion of the second sequence of images.

20 Claims, 10 Drawing Sheets

US 11,931,206 B2

ULTRASOUND IMAGING SYSTEM AND METHOD FOR SAVING A SEQUENCE OF IMAGES AS A CINELOOP

FIELD OF THE INVENTION

This disclosure relates generally to a method and system of ultrasound imaging for saving a sequence of images as a cineloop.

BACKGROUND OF THE INVENTION

Conventional ultrasound imaging systems can often be configured to store a sequence of images as a cineloop in either a retrospective storage mode or a prospective storage mode. Ultrasound imaging systems typically include both a volatile memory, also called an image buffer, and non-volatile memory for more-permanent storage. The volatile memory is a memory that retains its data only while the device is powered. As soon as the device is powered-down, the data in the volatile memory is lost. The non-volatile memory, on the other hand, retains its data even when the power is removed. Volatile memory is therefore well-suited for use as an image buffer that is frequently overwritten. However, if it is desired to save data more permanently, then the non-volatile memory should be used.

In the prospective storage mode, conventional ultrasound imaging systems will store a sequence of images as a cineloop that is a fixed length after a storage button has been pressed. The fixed length may be either a defined number of seconds after the storage button has been pressed or a defined number of cardiac cycles after the storage button has been pressed. In the retrospective storage mode, conventional ultrasound imaging systems will store a sequence of images that is the last elapsed defined number of cycles or seconds. For example, a conventional system may be configured to store a sequence of images corresponding to the last two cardiac cycles of the patient in a retrospective storage mode.

Clinicians tend to use the retrospective storage mode most frequently because the clinicians are able to see the images that were acquired before committing them to non-volatile memory. It is common for the clinician to move/reposition the ultrasound probe until they are satisfied with the quality of the images being acquired before pressing the store button in a retrospective storage mode. However, there is a problem with the retrospective storage mode on conventional ultrasound imaging systems. Many quantitative measurement tools require a minimum amount of data to function properly. That is, many quantitative measurement tools require a sequence of images that meets or exceeds a length threshold in non-volatile memory. For example, many cardiac analysis and measurement tools require an ultrasound image sequence corresponding to at least one full cardiac cycle and many cardiac analysis and measurement tools require a sequence of images corresponding to at least two full cardiac cycles. With conventional ultrasound imaging systems, while in a retrospective storage mode, clinicians oftentimes attempt to store a sequence of images that is shorter than a length threshold. For example, if the sequence of images in the volatile memory is less than the length threshold when the clinician initiates the store command in a retrospective storage mode, conventional ultrasound imaging systems will store that sequence of images as a cineloop in the non-volatile memory. This is problematic because the sequence of images stored as a cineloop in the non-volatile memory is too short to be used with the cardiac analysis and measurement tools. At a minimum, the clinician will need to perform an additional acquisition to acquire and store a sequence of images that meets or exceeds the length threshold. Oftentimes, the clinician will remove the probe from the patient after storing the sequence of images as a cineloop in the non-volatile memory. The clinician will then need to spend additional time to correctly position and orient the ultrasound probe in order to acquire a new sequence of images of the desired location. If the clinician has completed the examination procedure before identifying that the sequence of images stored in non-volatile memory is too short, the clinician will need to schedule another examination for the patient in order to acquire a sequence of images that meets or exceeds the length threshold. For at least these reasons, there is a need for an improved method and ultrasound imaging system for performing an ultrasound examination.

BRIEF DESCRIPTION OF THE INVENTION

The above-mentioned shortcomings, disadvantages and problems are addressed herein which will be understood by reading and understanding the following specification.

In an embodiment, a method of ultrasound imaging includes initiating a live ultrasound scanning session. The method includes acquiring and saving a first sequence of images in a volatile memory during the live ultrasound scanning session. The method includes receiving a store command while in a retrospective image capture mode during the live ultrasound scanning session. The method includes detecting, with a processor, that the first sequence of images does not meet a length threshold and, in response to said detecting that the first sequence of images does not meet the length threshold, automatically continuing to acquire a second sequence of images after said receiving the store command. The method includes detecting, with the processor, that the combination of the first sequence of images and the second sequence of images meets or exceeds the length threshold. The method includes saving a third sequence of images as a cineloop in a non-volatile memory, wherein the third sequence of images includes both at least a portion of the first sequence of images and at least a portion of the second sequence of images, and wherein the third sequence of images meets or exceeds the length threshold.

In an embodiment, an ultrasound imaging system includes an ultrasound probe, a user interface, a volatile memory, a non-volatile memory, a display device, and a processor. The processor is configured to receive an initiation of a live ultrasound scanning session and control the ultrasound probe to acquire a first sequence of images. The processor is configured to save the first sequence of images in the volatile memory during the live ultrasound scanning session and receive a store command via the user interface while in a retrospective image capture mode during the live ultrasound scanning session. The processor is configured to detect that the first sequence of images does not meet a length threshold and, in respond to detecting that the first sequence of images does not meet the length threshold, automatically control the ultrasound probe to continue to acquire a second sequence of images after receiving the store command. The processor is configured to detect that the combination of the first sequence of images and the second sequence of images meets or exceeds the length threshold. The processor is configured to save a third sequence of images as a cineloop in the non-volatile memory, wherein the third sequence of images includes both at least a portion of the first sequence of images and at least a portion of the second sequence of images, and wherein the third sequence of images meets or exceeds the length threshold.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized, and that logical, mechanical, electrical and other changes may be made without departing from the scope of the embodiments. The following detailed description is, therefore, not to be taken as limiting the scope of the invention.

Figure 1:
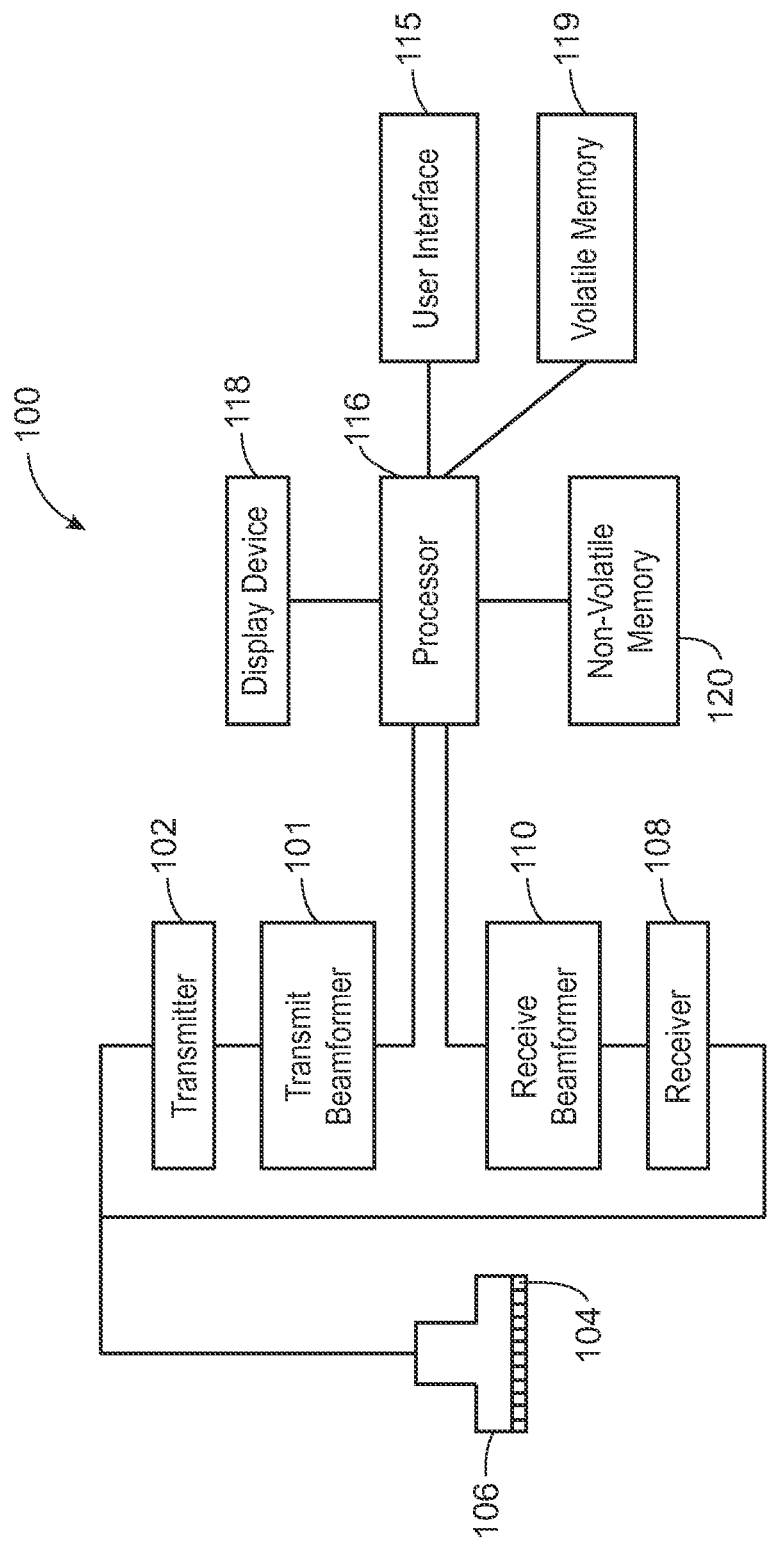
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within an ultrasound probe 106 to emit pulsed ultrasonic signals into a body (not shown). The ultrasound probe 106 may be a linear probe, a curved linear probe, a 2D array, a mechanical 3D/4D probe, or any other type of ultrasound probe capable of acquiring ultrasound data. Still referring to FIG. 1, the pulsed ultrasonic signals are back-scattered from structures in the body, like blood cells or muscular tissue, to produce echoes that return to the elements 104. The echoes are converted into electrical signals by the elements 104 and the electrical signals are received by a receiver 108. The electrical signals representing the received echoes are passed through a receive beamformer 110 that outputs ultrasound data. According to some embodiments, the ultrasound probe 106 may contain electronic circuitry to do all or part of the transmit and/or the receive beamforming. For example, all or part of the transmit beamformer 101, the transmitter 102, the receiver 108 and the receive beamformer 110 may be situated within the ultrasound probe 106. The terms "scan" or "scanning" may also be used in this disclosure to refer to acquiring data through the process of transmitting and receiving ultrasonic signals. The terms "data" or "ultrasound data" may be used in this disclosure to refer to either one or more datasets acquired with an ultrasound imaging system. A user interface 115 may be used to control operation of the ultrasound imaging system 100, including, to control the input of patient data, to set an acquisition preset, or to change a display parameter, and the like. The user interface 115 may include components such as a keyboard, a mouse, a track ball, a track pad, a touch screen, a multi-touch screen, and the like.

The ultrasound imaging system 100 also includes a processor 116 to control the transmit beamformer 101, the transmitter 102, the receiver 108 and the receive beamformer 110. The processor 116 is in electronic communication with the ultrasound probe 106. The processor 116 may control the ultrasound probe 106 to acquire data. The processor 116 controls which of the elements 104 are active and the shape of a beam emitted from the ultrasound probe 106. The processor 116 is also in electronic communication with a display device 118, and the processor 116 may process the data into images or values for display on the display device 118. Each image may represent a single frame of ultrasound data. For purposes of this disclosure, the term "image" may refer to either the image that is displayed on the display device 118 or the ultrasound data that is used to generate the displayed image. The term "image" may also be used to refer to either raw ultrasound data that is used to generate the displayed image or processed ultrasound data that is used to generate the displayed image. The display device 118 may comprise a monitor, an LED display, a cathode ray tube, a projector display, or any other type of apparatus configured for displaying an image. Additionally, the display device 118 may include one or more separate devices. For example, the display device 118 may include two or more monitors, LED displays, cathode ray tubes, projector displays, etc. The display device 118 may also be a touchscreen. For embodiments where the display device 118 is a touchscreen, the touchscreen may function as an input device, and it may be configured to receive touch or touch gesture inputs from a user. For purposes of this disclosure, the term "electronic communication" may be defined to include both wired and wireless connections. The processor 116 may include a central processor (CPU) according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, an FPGA, and a graphic board. According to another embodiment, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For purposes of this disclosure, the term "real-time" will additionally be defined to include an action occurring within 2 seconds. For example, if data is acquired, a real-time display of that data would occur within 2 seconds of the acquisition. Those skilled in the art will appreciate that most real-time procedures/processes will be performed in substantially less time than 2 seconds. The data may be stored temporarily in a buffer (not shown) during a scanning session and processed in less than real-time in a live or off-line operation.

Some embodiments of the invention may include multiple processors (not shown) to handle the processing tasks. For example, a first processor may be utilized to demodulate and decimate the RF signal while a second processor may be used to further process the data prior to displaying an image. It should be appreciated that other embodiments may use a different arrangement of processors.

The ultrasound imaging system 100 includes a volatile memory 119 and a non-volatile memory 120. The volatile memory 119 is a memory that retains its data only while the device is powered. As soon as the device is powered-down, the data in the volatile memory 119 is lost. The non-volatile memory 120, on the other hand, retains its data even when the power is removed. Therefore, the volatile memory 119 is well-suited for storing data that the processor 116 needs to access in real-time, while the non-volatile memory 120 is well-suited for permanent data storage. The volatile memory 119 may be used to operate in situations that require fast response times to read/write to the volatile memory 119. The non-volatile memory 120 may be used to operate in situations that require the ability to store larger amounts of data and/or data for which longer-term storage is desired.

The volatile memory 119 and the non-volatile memory 120 may take any suitable form. For instance, the volatile memory 119 may use any current or future technology for implementing random access memory (RAM), dynamic random access memory (DRAM)), or cache memory. Non-limiting examples of volatile memory include CPU memory and GPU memory. The non-volatile memory 120 may use any current or future technology for implementing RAM, DRAM or read-only memory (ROM) that retains the ability to store data while in an unpowered state. Non-limiting examples of non-volatile memory include a memory chip, a hard disk drive, an optical disk drive, or solid state memory, such as a flash memory or a solid-state drive (SSD).

The ultrasound imaging system 100 may continuously acquire data at a given frame-rate or volume-rate. Images generated from the data may be refreshed at a similar frame-rate or volume-rate. The processor 116 may store several seconds of ultrasound data in the volatile memory 119. The volatile memory 119 may also be referred to as an image buffer. The volatile memory 119 may be used as a "rolling buffer" as ultrasound data is being acquired. For example, according to various embodiments, several seconds of the most-recently acquired ultrasound data may be stored in the volatile memory 119. As additional ultrasound data is acquired, the most-recently acquired ultrasound data will replace the oldest data in the volatile memory 119. The amount of ultrasound data that can be stored in the volatile memory 119 will depend on the size of the volatile memory 119 and the other system-specific and/or mode-specific needs placed on the volatile memory 119 by the ultrasound imaging system 100.

According to various embodiments, the processor 116 may selectively store or save some or all of the data in the volatile memory 119 in the non-volatile memory 120 for longer-term storage. For purposes of this disclosure, the terms "store" and "save" will be used interchangeably. For example, in response to a user command, the processor 116 may store, in the non-volatile memory 120, some or all of the ultrasound data currently in the volatile memory 119. For instance, the user may indicate that some or all of the ultrasound data in the volatile memory 119 should be saved as part of an examination procedure. According to an embodiment, some or all of the ultrasound data in the volatile memory 119 may be stored in the non-volatile memory 120 as a Digital Imaging and Communications in Medicine (DICOM) object as part of an examination procedure for a patient. Some or all of the ultrasound data in the volatile memory 120 may be stored in a format other than as a DICOM object according to various embodiments. It should be appreciated by those skilled in the art that the non-volatile memory 120 may be used to store data other than ultrasound data as well. For example, the non-volatile memory 120 may be used to store instructions that may be accessed and implemented by the processor 116.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams or images are stored and timing information indicating a time at which the data was acquired in memory may be recorded. The modules may include, for example, a scan conversion module to perform scan conversion operations to convert the images from coordinates beam space to display space coordinates. A video processor module may be provided that reads the images from a memory and displays the images in real time while a procedure is being carried out on a patient. A video processor module may store the images in an image memory, from which the images are read and displayed.

Figure 2:
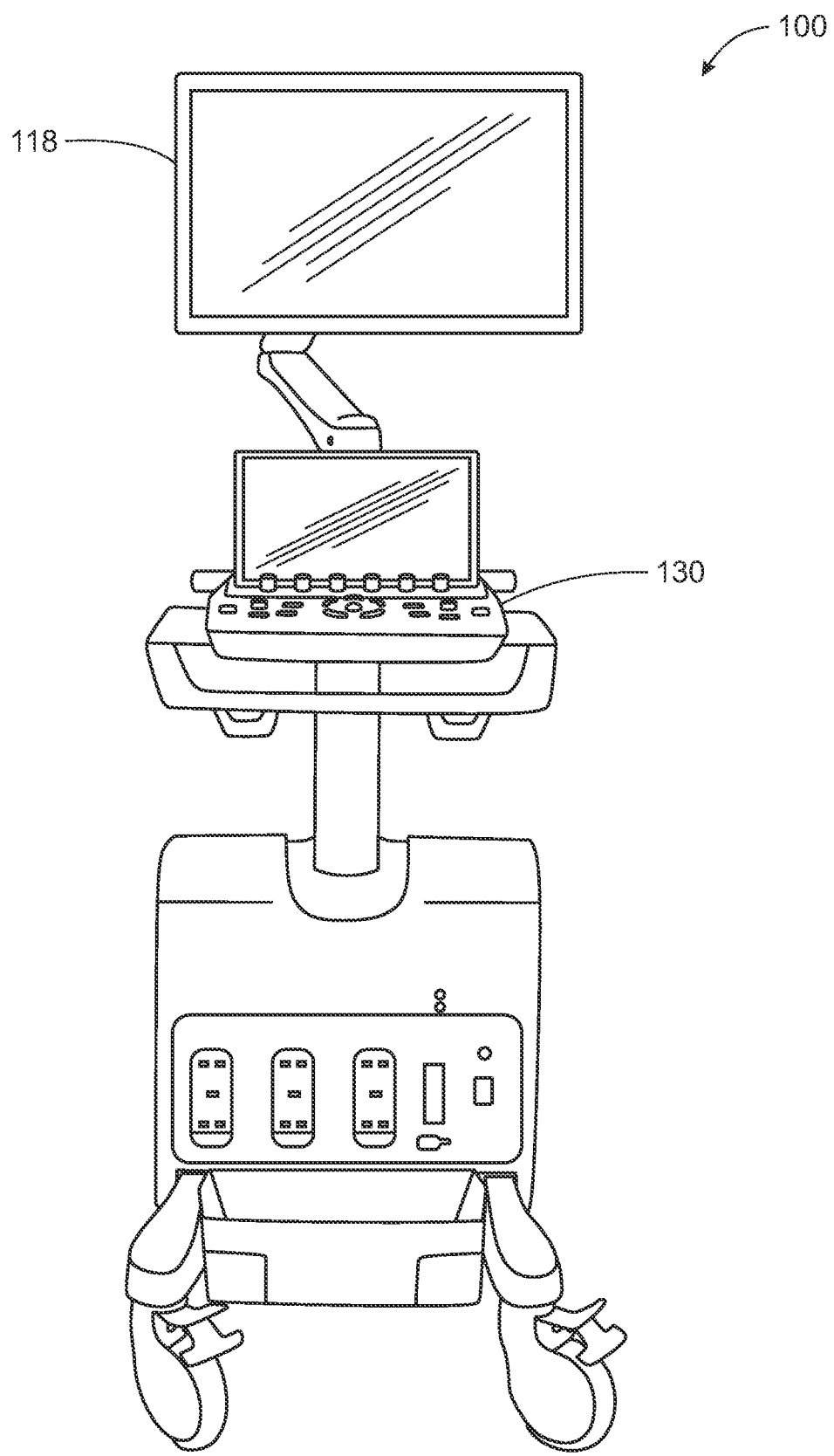
FIG. 2 is a representation of an ultrasound imaging system in accordance with an embodiment.

FIG. 2 is a representation of the ultrasound imaging system 100 in accordance with an embodiment. The ultrasound imaging system 100 is a console-based ultrasound imaging system. The display device 118 and a control panel 130 are shown on the ultrasound imaging system 100 illustrated in FIG. 2.

Figure 3:
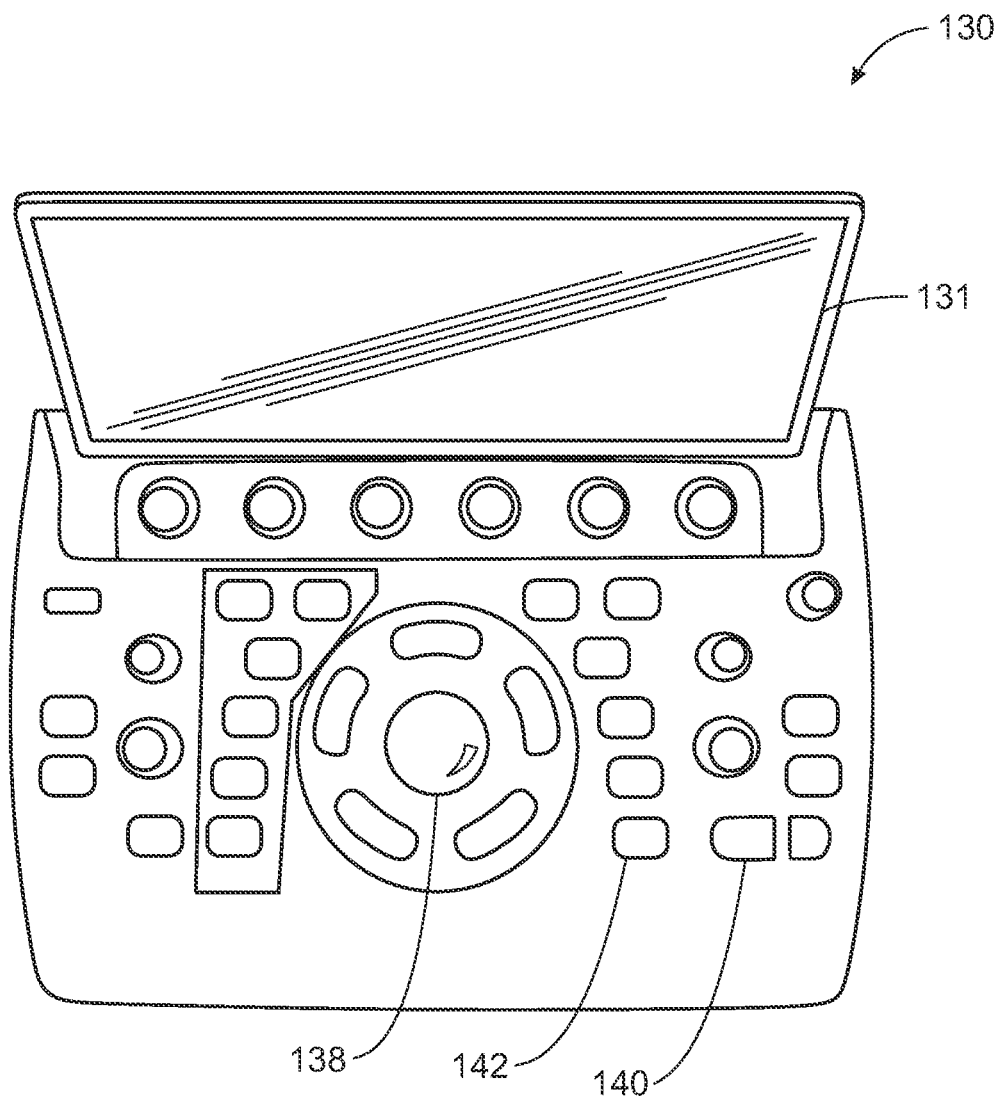
FIG. 3 is a representation of a control panel of an ultrasound imaging system in accordance with an embodiment.

FIG. 3 is a representation of the control panel 130 in accordance with an embodiment. The control panel 130 includes a touchscreen 131, a trackball 138, a freeze button 140, and a store button 142. The control panel 130 also includes other controls that are not labeled on FIG. 3.

The trackball 138 may be used to control the position of a cursor or pointer displayed on the display device 118 and to interact with a graphical user interface (GUI) displayed on the display device 118. The user may interact with the GUI via interactions with the control panel 130 or via interactions, such as touches or gestures, with the touchscreen 131 according to various embodiments.

The freeze button 140 is configured to stop the acquisition of ultrasound data. After the freeze button 140 is pressed during an acquisition, no additional ultrasound data is added to the volatile memory 119. The store button 142 is used to save an image or a sequence of images located in volatile memory 119 to the non-volatile memory 120.

Figure 4:
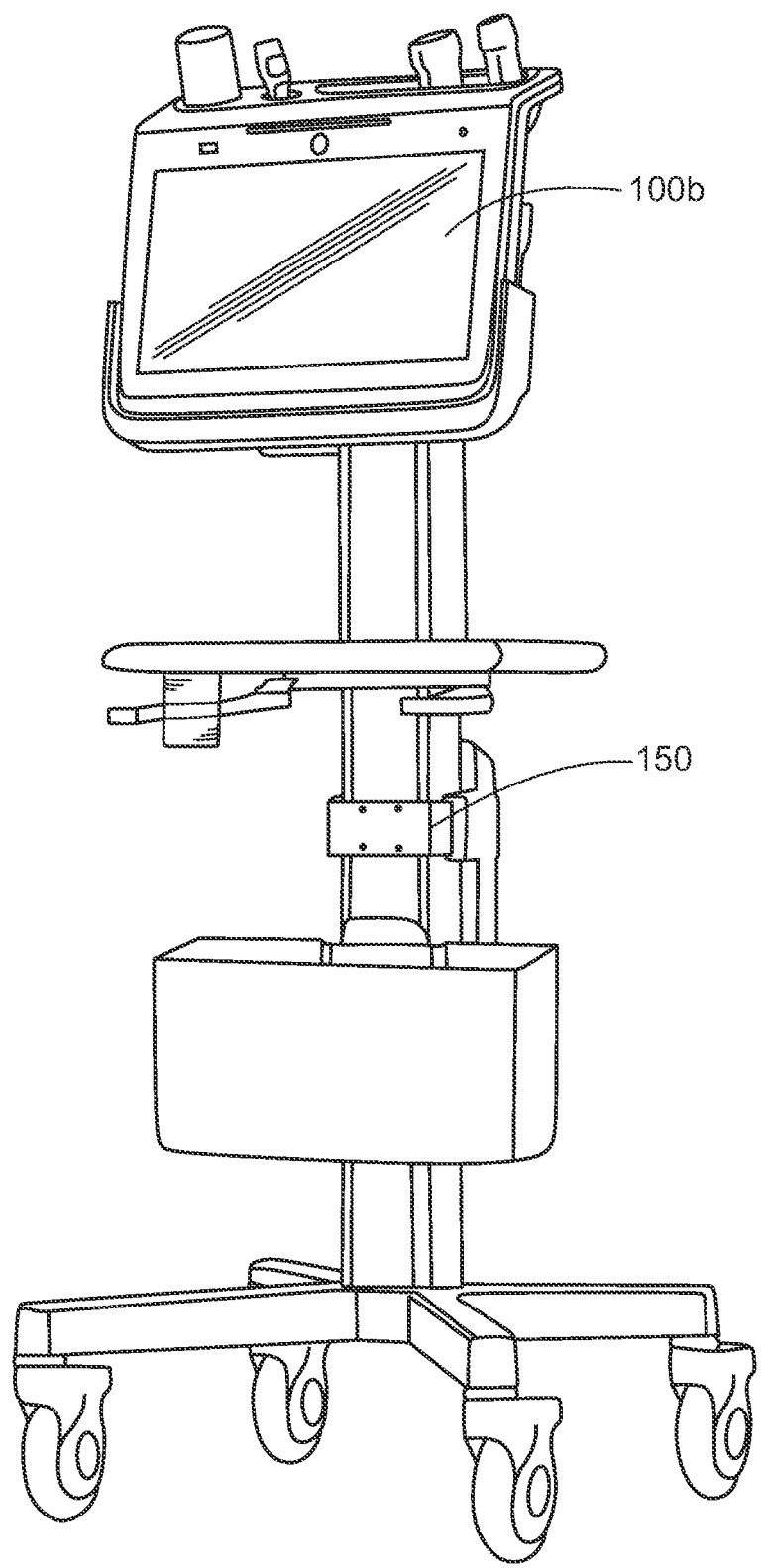
FIG. 4 is a representation of an ultrasound imaging system in accordance with an embodiment.

According to other embodiments ultrasound imaging systems with different form factors may be used. For example, the components schematically represented in FIG. 1 may be configured in an ultrasound imaging system with a different form factor than the one shown in FIG. 2. For example, the ultrasound imaging system 100 may be configured as a hand-held or hand-carried ultrasound imaging system, as a laptop or tablet-based ultrasound imaging system, or as a portable ultrasound imaging system that is configured to be removably mounted to a cart. FIG. 4 shows an ultrasound imaging system 100b according to an exemplary embodiment. The ultrasound imaging system 100b is configured to be removably mounted to a cart 150. The ultrasound imaging system 100b may be used while attached to the cart 150 or the while detached from the cart 150. While not labeled on FIG. 4, the ultrasound imaging system 100b may include all of the same components schematically represented in FIG. 1.

Figure 5:
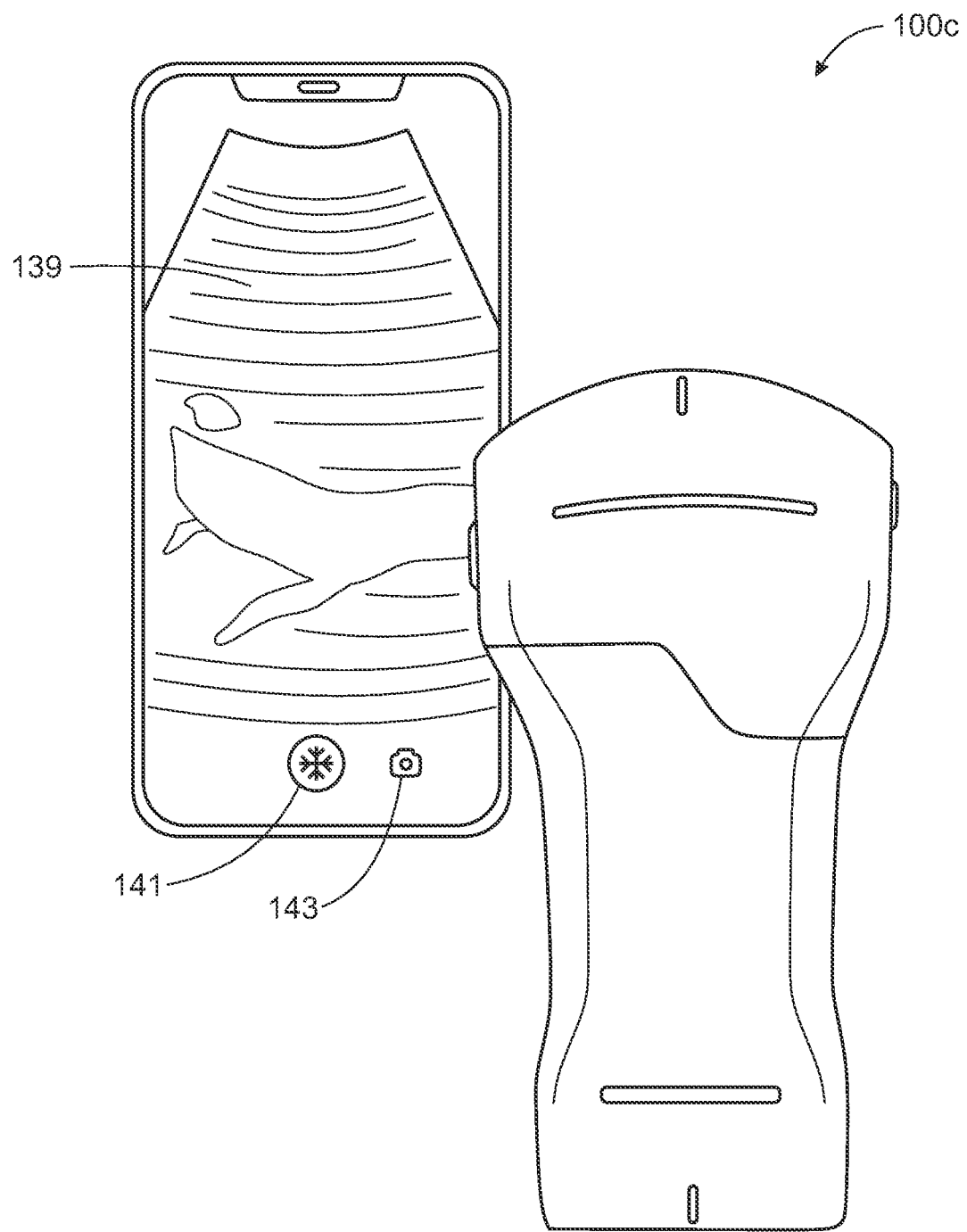
FIG. 5 is a representation of an ultrasound imaging system in accordance with an embodiment.

FIG. 5 shows an ultrasound imaging system 100c in accordance with an exemplary embodiment. The ultrasound imaging system 100c is a hand-held ultrasound imaging system with a form factor similar to that of a smartphone. While not labeled, the ultrasound imaging system 100c may include some or all of the same components schematically represented in FIG. 1. According to an exemplary embodiment, the ultrasound imaging system 100c includes a touchscreen 139. The touchscreen 139 performs the functions of both the display device 118 (shown in FIG. 1) and the user interface 115 (shown in FIG. 1). Both the ultrasound imaging system 100b, shown in FIG. 4, and/or the ultrasound imaging system 100c, shown in FIG. 5, include a touchscreen as part of the user interface 115. Some of control functions associated with the control panel 130, shown in FIG. 3, may be performed using a GUI displayed on the touchscreen of either the ultrasound imaging system 100b or the ultrasound imaging system 100c. For example, the ultrasound imaging system 100c includes a freeze button 141 and a store button 143 that may be actuated based on a touch input via the touchscreen.

Figure 6:
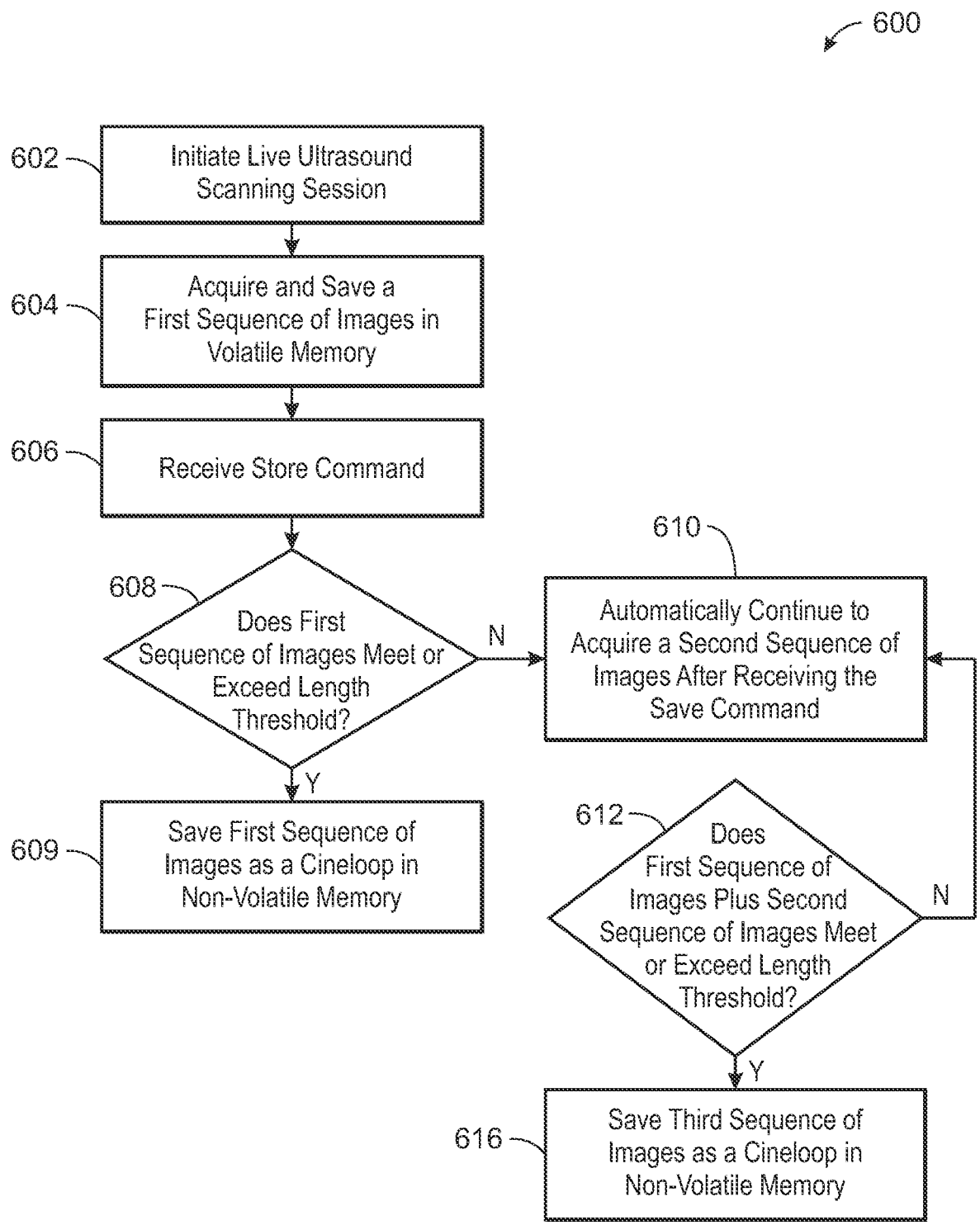
FIG. 6 is a flow chart of a method in accordance with an embodiment.

FIG. 6 is a flow chart of a method 600 in accordance with an exemplary embodiment. The individual blocks of the flow chart represent steps that may be performed in accordance with the method 600. Additional embodiments may perform the steps shown in a different sequence and/or additional embodiments may include additional steps not shown in FIG. 6. The technical effect of the method 600 is the storage of a third sequence of images in the non-volatile memory 120, where the third sequence of images meets or exceeds a length threshold. The term cineloop may be used in this disclosure to describe either a sequence of images being displayed as a loop or the ultrasound data for a sequence of images that may be displayed as a loop. The method 600 will be described according to an embodiment where it is performed with the ultrasound imaging system 100 shown in FIG. 1. However, it should be appreciated by those skilled in the art that the method 600 may be performed with other ultrasound imaging systems according to various embodiments, including the ultrasound imaging systems 100b and 100c, shown in FIG. 4 and FIG. 5, respectively. The method 600 will be described in detail hereinafter.

At step 602, a user initiates a live ultrasound scanning session on the ultrasound imaging system 100 by using the ultrasound probe 106 to acquire live, or real-time, ultrasound data. According to some embodiments, the user may need to perform other steps such as selecting the patient, selecting a scan mode and/or protocol, and selecting the probe in order to initiate the scanning session. According to other embodiments, the user may initiate the session by simply beginning to scan and acquire live ultrasound images. Once the live ultrasound scanning session has been initiated at step 602, images generated based on the ultrasound data acquired during the live ultrasound scanning session are displayed, in real-time, on the display device 118. As discussed previously, the image displayed on the display device 118 represents the image that was most-recently acquired during the live ultrasound scanning session, and the image displayed on the display device 118 may be refreshed with an updated image as each additional image, or frame, of ultrasound data is acquired during a live ultrasound scanning session.

At step 604, a first sequence of images is acquired and saved in the volatile memory 119. According to an exemplary embodiment, the processor 116 may be configured to start saving images into the volatile memory 119 as soon as the live ultrasound scanning session has been initiated at step 602. Each ultrasound image may include a time stamp indicating the time of acquisition. According to an exemplary embodiment, the volatile memory 119 may be configured to be used as a rolling buffer that saves the last N seconds of ultrasound images. From time zero to N, all of the images acquired as part of the live ultrasound scanning session may be saved in the volatile memory 119. However, once more than N seconds of ultrasound images have been acquired, more-recently acquired ultrasound images will replace the oldest ultrasound images in the volatile memory 119. This way, the volatile memory 119 always includes the most-recently acquired ultrasound images that were acquired as part of the live ultrasound scanning session. During the process of live scanning, the oldest images in the volatile memory 119 are continuously being replaced by the most-recently acquired images.

At step 606, the processor 116 receives a store command that was input through the user interface 115. The store command may be input through the activation of a control on the control panel 130 shown in FIG. 3, such as the store button 142, or according to the activation of a different control. For example, according to various embodiments, the store command may be input based on interaction with a GUI displayed on a touchscreen.

Next, at step 608, the processor compares the length of the first sequence of images in the volatile memory 119 to a length threshold. According to some embodiments, the length of the first sequence of images needs to meet the length threshold. According to other embodiments, the length of the first sequence needs to exceed the length threshold. The length threshold may include one of the following: an amount of time; a specified number of cardiac cycles; the specified number of cardiac cycles plus a first designated amount of time before the specified number of cardiac cycles; the specified number of cardiac cycles plus a second designated amount of time after the specified number of cardiac cycles, or the specified number of cardiac cycles plus both the first designated amount of time before the specified number of cardiac cycles and the second designated amount of time after the specified number of cardiac cycles.

If ECG data is available, then the processor 116 may be configured to use the ECG data to determine the number of cardiac cycles represented by the first sequence of images. However, according to many embodiments, ECG data corresponding to the first sequence of images may not be available. The processor 116 may be configured to determine the cardiac phase using other techniques. For instance, the processor 116 may be configured to use tissue velocity information, determined from the ultrasound data, in order to determine a cardiac phase associated with each of the images. According to other embodiments without ECG data, the processor 116 may be configured to use artificial intelligence, such as a deep learning neural network, to identify the cardiac phase of each of the images in the sequence of images. For example, the processor 116 may be configured to implement a deep learning neural network, or other types of artificial intelligence, in order to identify the cardiac phase of each of the images in the sequence of images. The processor 116 may be configured to use other types of artificial intelligence according to various embodiments. Then, based on the determined cardiac phase, the processor 116 may be configured to determine the number of cardiac cycles represented by the first sequence of images. Then, the processor 116 may compare the length of the first sequence of images (in cardiac cycles) to the threshold length. The threshold length may be a predetermined length or, according to other embodiments, the threshold length may be user configurable. For example, the user may be able to adjust the threshold length via inputs through the user interface 115 according to various embodiments.

The threshold length may be an integral number of cardiac cycles, such as one cardiac cycles, two cardiac cycles, three cardiac cycles, etc. The threshold length may be a specific number of cardiac cycles plus a first designated amount of time before the specified number of cardiac cycles. For example, the threshold length may be one cardiac cycle plus N seconds before the cardiac cycle, two cardiac cycles plus N seconds before the two cardiac cycles, three cardiac cycles plus N seconds before the three cardiac cycles, etc., where N is a first designated amount of time in seconds.

The threshold length may be a specific number of cardiac cycles plus a second designated amount of time after the specified number of cardiac cycles. For example, the threshold length may be one cardiac cycle plus X seconds after the cardiac cycle, two cardiac cycles plus X seconds after the two cardiac cycles, three cardiac cycles plus X seconds after the three cardiac cycles, etc., where X is a second designated amount of time in seconds.

The threshold length may be a specific number of cardiac cycles plus a first designated amount of time before the specified number of cardiac cycles and a second designated amount of time after the specified number of cardiac cycles. For example, the threshold length may be one cardiac cycle plus N seconds before the cardiac cycle and X second after the cardiac cycle, two cardiac cycles plus N seconds before the two cardiac cycles and X second after the two cardiac cycles, three cardiac cycles plus N seconds before the three cardiac cycles and X second after the three cardiac cycles, etc., where N is a first designated amount of time in seconds and X is a second designated amount of time.

According to various embodiments, the length threshold may be a designated amount of time. The length threshold may be an amount of time expressed in seconds. The length threshold may be any amount of time according to various embodiments, but for most applications it is desired to have the amount of time (of the length threshold) selected so that the sequence of images clearly shows one or more complete cardiac cycles and does not take an unnecessarily long time to acquired. For example, according to various embodiments, the length threshold may be an amount of time, such as, 1 s, 1.5 s, 2 s, 2.5 s, 3 s, 3.5 s, 4 s, etc. Those skilled in the art should appreciate that the amount of time may be an amount of time that is different than the exemplary times listed above.

If, at step 608, the first sequence of images meets or exceeds the length threshold, then the method proceeds to step 609, where the first sequence of images is stored as a cineloop in the non-volatile memory 120.

If, at step 608, the first sequence of images does not meet or exceed the length threshold, then the method 600 advances to step 610. At step 610, in response to detecting that the first sequence of images does not meet the length threshold, the processor 116 automatically controls the ultrasound probe 106 to continue to acquire a second sequence of images after receiving the store command. According to an embodiment, it is anticipated that the processor 116 will be able to compare the length of the first sequence of images stored in the volatile memory 119 to the length threshold at step 608 very quickly. Therefore, if the method 600 advances to step 610 (due to the first sequence of images not meeting the length threshold), it is anticipated that the processor 116 will implement step 610 without any gap in the scanning session. In other words, according to various embodiments, there will not be any discernable gap in time between the end of the first sequence of images and the beginning of the second sequence of images. In other words, the time between the last image in the first sequence of images and the first image in the second sequence of images will be the same as between all of the other adjacent images in the first sequence of images. In other words, the processor 116 will maintain the frame-rate that was used during the acquisition of the first sequence of images during the transition from acquiring the first sequence of images to acquiring the second sequence of images.

The processor 116 may be configured to control the ultrasound probe 106 to continue acquiring the second sequence of images until the combination of the first sequence of images and the second sequence of images meets or exceeds the length threshold. According to some embodiments, the combination of the first sequence of images and the second sequence of images needs to meet the length threshold. According to other embodiments, the combination of the first sequence of images and the second sequence of images needs to exceed the length threshold. For example, at step 612, the processor 116 compares the combination of the first sequence of images and the second sequences of images to the length threshold that was used during step 608. If the combination of the first sequence of images and the second sequences of images does not meet or exceed the length threshold, the method 600 returns to step 610 where the processor 116 controls the ultrasound probe 106 to automatically continue to acquire the second sequences of images. If, at step 612, the combination of the first sequence of images and the second sequences of images meets or exceeds the length threshold, then the method 600 advances to step 616. By iteratively performing step 610 and step 612, the processor 116 controls the ultrasound probe 106 to continue acquiring the second sequence of images until the combination of the first sequence of images and the second sequences of images meets or exceeds the length threshold.

At step 616, the processor 116 saves a third sequence of images as a cineloop in the non-volatile memory 120. The third sequence of images includes at least a portion of the first sequence of images and at least a portion of the second sequence of images. The third sequence of images meets or exceeds the length threshold. According to an embodiment, the third sequence of images may include all of the first sequence of images and all of the second sequence of images. According to an embodiment, the third sequence of images may include a portion of the first sequence of images and all of the second sequence of images. According to an embodiment, the third sequence of images may include all of the first sequence of images and a portion of the second sequence of images. According to an embodiment, the third sequence of images may include a portion of the first sequence of images and a portion of the second sequence of images. The third sequence of images, which is stored as a cineloop in the non-volatile memory 120, meets or exceeds the length threshold.

The processor 116 may be configured to automatically save the third sequence of images as a cineloop in the non-volatile memory 120 in response to detecting that the combination of the first sequence of images and the second sequence of images meets or exceeds the length threshold. The processor 116 may be configured to automatically save the third sequence in response to detecting that the combination of the first sequence of images and the second sequence of images meets the length threshold. According to an exemplary embodiment, the third sequence of images may include both all of the first sequence of images and all of the second sequence of images. According to an embodiment, the processor 116 may be configured to automatically save the third sequence in response to detecting that the combination of the first sequence of images and the second sequence of images exceeds the length threshold. The third sequence of images, which is saved as the cineloop, may include both all of the first sequence of images and all of the second sequence of images. Or, according to other embodiments where the combination of the first sequence of images and the second sequence of images exceeds the length threshold, the third sequence of images may not include all of the first and/or second sequences of images.

For example, according to an embodiment, the third sequence of images that is saved as a cineloop to the non-volatile memory 120 may exceed the length of the length threshold. Therefore, the processor 116 may be configured to select, as the third sequence of images, only a subset of the images in the combination of the first and second sequences of images. For example, the processor 116 may be configured to select, as the third sequence of images: only of subset of the first sequence of images plus all of the second sequence of images; only a subset of the second sequence of images plus all of the first sequence of images; or a subset of both the first sequence of images and the second sequences of images. It is anticipated that the processor 116 will be configured to select, for the third sequence of images, consecutive images from the combination of the first and second sequences of images. If only a portion of images in either the first sequence of images and/or the second sequence of images are saved as the third sequence of images, the saved images in the third sequence of images will represent consecutively acquired images and the images that are not saved will be from either an initial portion (in terms of time of acquisition) of the first sequence of images and/or a final portion (in terms of time of acquisition) of the second sequence of images. The third sequence of images therefore includes a consecutively acquired sequence of images from both the first sequence of images and the second sequence of images.

Since the third sequence of images meets or exceeds the length threshold, saving the third sequence of images as a cineloop in the non-volatile memory 120 results in a cineloop that meets or exceeds the length threshold. This is advantageous because the cineloop saved in the non-volatile memory 120 meets/exceeds the length threshold. As discussed previously, many quantitative measurement tools require a cineloop that meets or exceeds a length threshold in order to work properly. In other words, many quantitative tools require a sequence of images that meets or exceeds the length threshold. For example, many cardiac analysis and measurement tools require an ultrasound image sequence corresponding to at least one full cardiac cycle and many cardiac analysis and measurement tools require a sequence of images corresponding to at least two full cardiac cycles. The method 600 ensures that the sequence of images saved to the non-volatile memory 120 meets or exceeds the length threshold. For example, if the first sequence of images meets or exceeds the length threshold, then the first sequence of images is saved to the non-volatile memory 120. And, on the other hand, if the first sequence of images is less than the length threshold, then, according to the method 600, the processor 116 saves a third sequence of images (including both at least a portion of the first sequence of images and at least a portion of the second sequence of images) as a cineloop in the non-volatile memory 120. According to this scenario, the third sequence of images saved as a cineloop in the non-volatile memory 120 meets or exceeds the length threshold. With conventional ultrasound imaging systems, when in a retrospective storage mode, clinicians oftentimes attempt to store a sequence of images that is shorter than a length threshold in the non-volatile memory 120. This is problematic because the sequence of images stored as a cineloop in the non-volatile memory 120 is too short to be used with the cardiac analysis and measurement tools. The technique of the method 600 is advantageous because it ensures, even while in a retrospective image capture mode that the cineloop stored in the non-volatile memory 120 meets or exceeds the length threshold. This, in turn, ensures that the cineloop is long enough to be used with any analysis and measurement tools, such as cardiac analysis and measurement tools. Furthermore, the method 600 reduces or eliminates the risk that the clinician will need to perform an additional acquisition, as part of either the same or a different scanning session, in order to successfully store a cineloop that meets or exceeds the length threshold. According to conventional methods, it is oftentimes necessary to perform multiple acquisitions and/or different scanning sessions in order to save a sequence of images that meets or exceeds the length threshold. If another acquisition and/or scanning session is required, then it is oftentimes necessary for the clinician to reposition and/or reorient the ultrasound probe 106 before performing the additional acquisition/scanning session. Repositioning the ultrasound probe 106 takes additional time, which is burdensome to both the patient and the clinician. The method 600 therefore saves time for both the patient and the clinician by reducing or eliminating the need to perform additional acquisitions to acquire and store cineloops that are long enough for the analysis and measurement tools.

According to an embodiment, the processor 116 may be configured to retrieve the cineloop from the non-volatile memory 120 and display the cineloop on the display device 118. According to other embodiments, a different processor, such as a processor associated with a remote workstation, may be configured to retrieve the cineloop from the non-volatile memory 120 and display the cineloop on a display device local to the remote workstation. The processor 116 may also be configured to calculate a metric, such as a metric calculated using cardiac analysis and measurement tools, based on the cineloop. Non-limiting examples of metrics that may be calculated based on the cineloop saved to the non-volatile memory 120 include ejection fraction, left ventricle dimension, right ventricle dimension, left ventricle end-diastolic volume, left ventricle end-systolic volume, right ventricle end-diastolic volume, right ventricle end-systolic volume, left atrial end-diastolic volume, left atrial end-systolic volume, right atrial end-diastolic volume, right atrial end-systolic volume, strain, and other metrics. According to various embodiments, the processor 116 may also be configured to determine the cardiac phase of images based on the cineloop saved to the non-volatile memory 120 or the heartrate of the patient based on the cineloop saved to the non-volatile memory 120.

Figure 7:
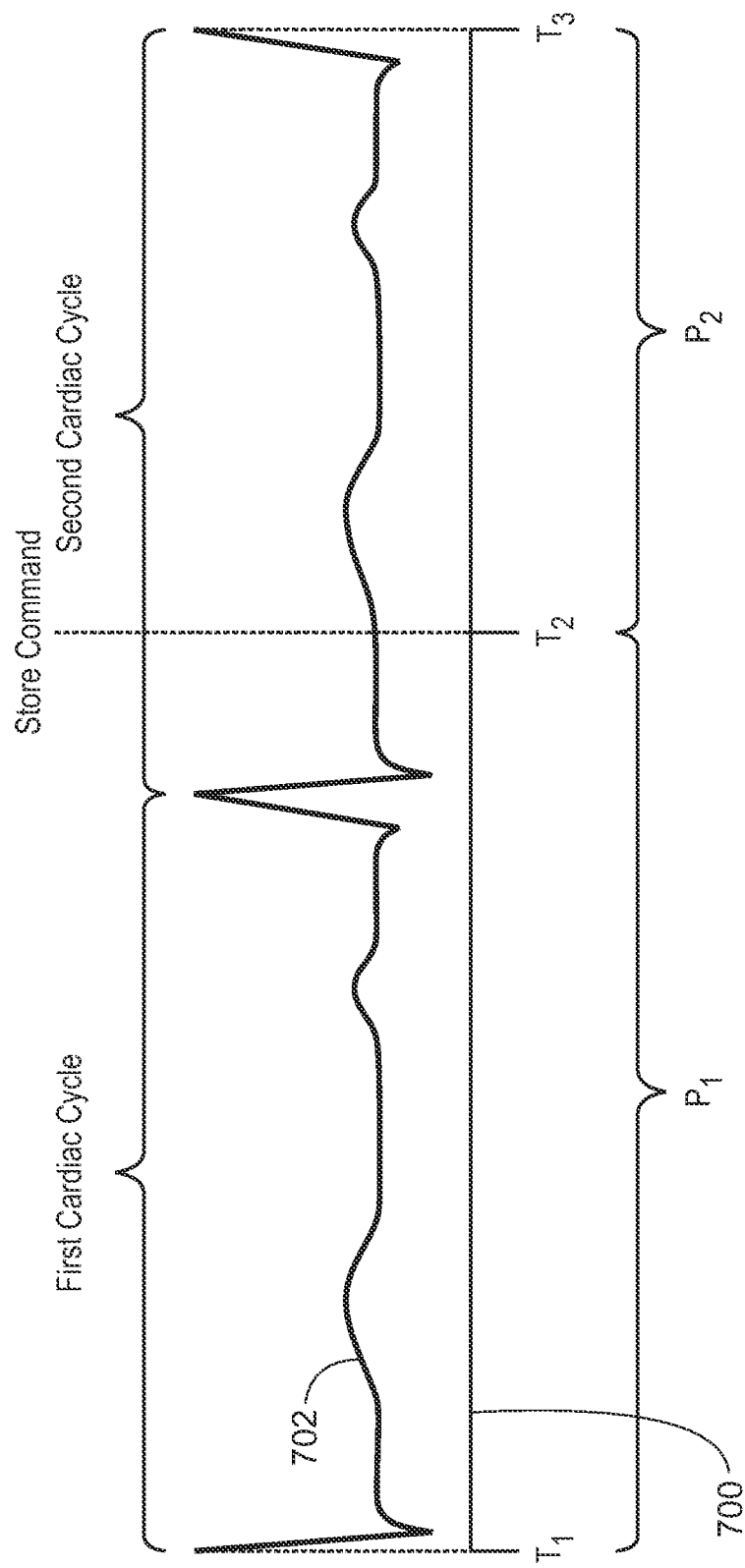
FIG. 7 is a representation of a time line in accordance with an embodiment.

FIG. 7 is a timeline in accordance with an exemplary embodiment. FIG. 7 includes a timeline 700 and an electrocardiogram (ECG) trace 702. The timeline 700 illustrates a first time period $P_1$ and a second time period $P_2$. The first time period $P_1$ and the second time period $P_2$ are both shown with respect to the timeline 700 and the ECG trace 702. FIG. 7 will be described with respect to the method 600, which was previously described with respect to FIG. 6. At step 602, the clinician initiates a live ultrasound scanning session. According to an embodiment, the first sequence of images are acquired during the first time period $P_1$, which corresponds to the time period from a time $T_1$ to a time $T_2$. The first sequence of images are saved in the volatile memory 119. At step 606, the processor 116 receives a store command at a time $T_2$ while the ultrasound imaging system is in a retrospective image capture mode. At step 608, the processor 116 compares the first sequence of images (i.e., the images acquired during the first time period $P_1$) to the length threshold. According to an exemplary embodiment, the length threshold may be two cardiac cycles. As is clear based on the ECG trace 702, the first time period $P_1$ is less than the threshold length (e.g., the first time period $P_1$ represents less than two complete cardiac cycles). So, since the first sequence of images is less than the length threshold at step 608, the processor 116 automatically continues to acquire a second sequence of images at the time $T_2$. As discussed previously with respect to FIG. 6, there is no gap or lag between the end of the first sequence of images and the start of the second sequence of images. On the example shown in FIG. 7, that processor 116 controls the ultrasound probe to continue acquiring the second sequence of images until the combination of the first sequence of images (acquired during the first time period $P_1$) and the second sequence of images (acquired during a second time period $P_2$) meets or exceeds the length threshold. According to an embodiment, the length threshold may be two cardiac cycles. Therefore, the processor 116 controls the ultrasound probe 106 to continue acquiring the second sequence of images until the sum of the first sequence of images and the second sequence of images meets or exceeds the length threshold of two cardiac cycles.

Viewing the ECG trace 702, it is apparent that the combination of the first time period $P_1$ and the second time period $P_2$ is two cardiac cycles. Therefore, the sum of the first sequence of images (acquiring during the first time period $P_1$) and the second sequence of images (acquiring during the second time period $P_2$) meets the length threshold of two cardiac cycles. The processor 116 may automatically save both the first sequence of images and the second sequence of images as a cineloop in the non-volatile memory 120. Thus, even though the ultrasound imaging system 100 was in a retrospective image capture mode, and the store command was received at the time $T_2$, the processor 116 controlled the ultrasound probe 106 to continue acquiring the second sequence of images from the time $T_2$ to the time $T_3$. At step 616, the processor 116 saves, as a cineloop, a third sequence of images (including both the first sequence of images and the second sequence of images according to an exemplary embodiment), which meets or exceeds the length threshold of two cardiac cycles.

Figure 8:
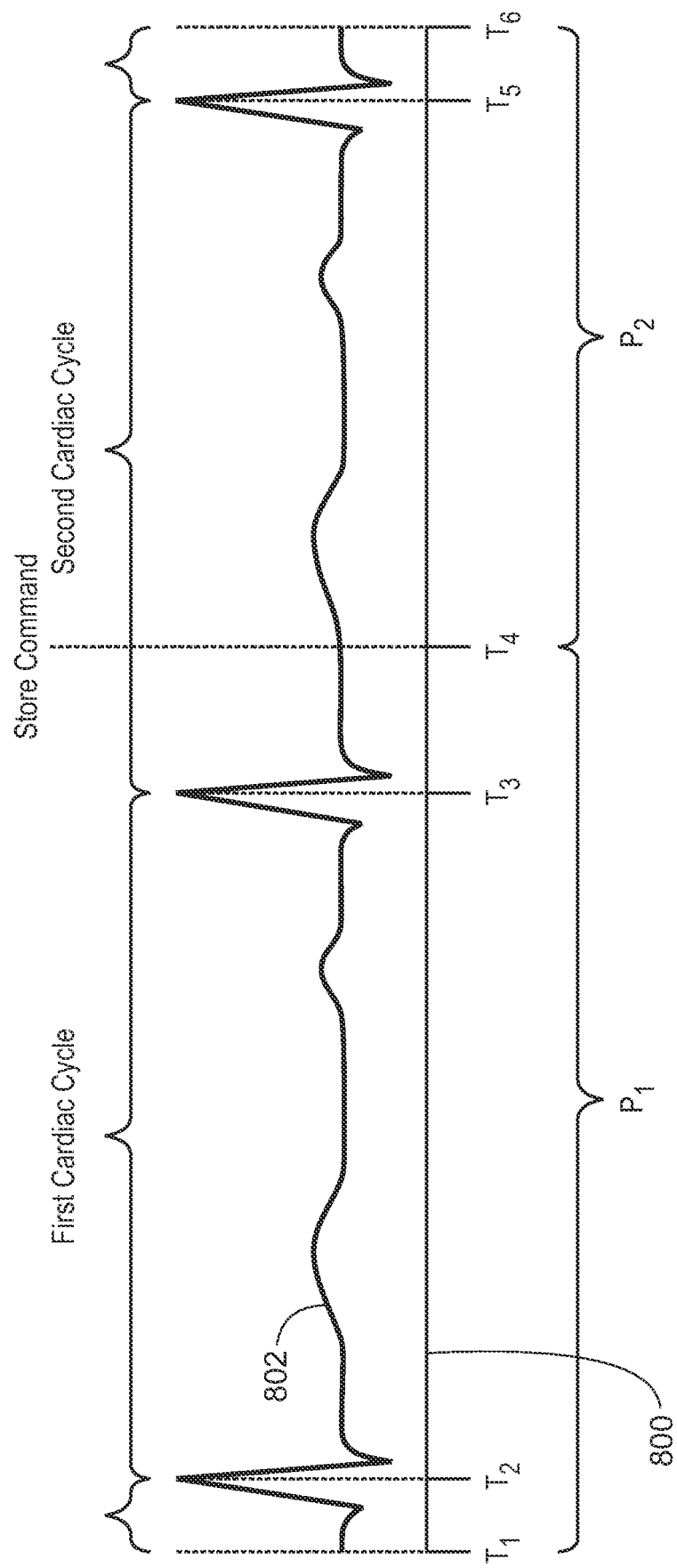
FIG. 8 is a representation of a time line in accordance with an embodiment.

FIG. 8 is a timeline in accordance with an exemplary embodiment. FIG. 8 includes a timeline 800 and an electrocardiogram (ECG) trace 802. The timeline 800 illustrates a first time period $P_1$ and a second time period $P_2$. The first time period $P_1$ and the second time period $P_2$ are both shown with respect to the timeline 800 and the ECG trace 802. FIG. 8 will be described with respect to the method 600, which was previously described with respect to FIG. 6. At step 602, the clinician initiates a live ultrasound scanning session. According to an embodiment, the first sequence of images are acquired during the first time period $P_1$, which corresponds to the time period from a time $T_1$ to a time $T_4$. The first sequence of images are saved in the volatile memory 119. At step 606, the processor 116 receives a store command at a time $T_4$ while the ultrasound imaging system is in a retrospective image capture mode. At step 608, the processor 116 compares the first sequence of images (i.e., the images acquired during the first time period $P_1$) to the length threshold. According to an exemplary embodiment, the length threshold may be two cardiac cycles plus both a designated time before the two cardiac cycles and a designated time after the two cardiac cycles. As is clear based on the ECG trace 802, the first period of time $P_1$ is less than the threshold length (e.g., the first sequence of images acquired during the first time period $P_1$ is less than two cardiac cycles plus both a designated time before the two cardiac cycles and a designated time after the two cardiac cycles). So, since the first sequence of images, which was acquired during the first time period $P_1$, is less than the length threshold at step 608, the processor 116 automatically continues to acquires a second sequence of images at the time $T_4$. As discussed previously with respect to FIG. 6, there is no gap or lag between the end of the first sequence of images and the start of the second sequence of images. On the example shown in FIG. 8, that processor 116 controls the ultrasound probe 106 to continue acquiring the second sequence of images until the combination of the first sequence of images (acquired during the first time period $P_1$) and the second sequence of images (acquired during a second time period $P_2$) meets or exceeds the length threshold. According to an embodiment, the length threshold may be two cardiac cycles plus both a designated time before the two cardiac cycles and a designated time after the two cardiac cycles. On FIG. 8, the first time period $P_1$ and the second time period $P_2$ meets or exceeds two cardiac cycles plus both a designated time before the two cardiac cycles and a designated time after the two cardiac cycles. For example, the time from time $T_1$ to $T_2$ is the designated time before the two cardiac cycles. The time from $T_5$ to $T_6$ is the designated time after the two cardiac cycles. The time from $T_2$ to $T_3$ is a first cardiac cycle and the time from $T_3$ to $T_5$ is a second cardiac cycle. The time from $T_2$ to $T_5$ is two cardiac cycles. Therefore, the time from $T_1$ to $T_6$ is equal to two cardiac cycles plus both a designated time before the two cardiac cycles and a designated time after the two cardiac cycles. Therefore, the processor 116 controls the ultrasound probe to continue acquiring the second sequence of images until the sum of the first sequence of images and the second sequence of images meets or exceeds the length threshold of two cardiac cycles.

Viewing the ECG trace 802, the time period between $T_2$ to $T_5$ is two cardiac cycles. The time from $T_1$ to $T_6$ is two cardiac cycles plus both a designated time before the two cardiac cycles and a designated time after the two cardiac cycles. Therefore, the sum of the first sequence of images (acquiring during the first time period $P_1$) and the second sequence of images (acquiring during the second time period $P_2$) meets the length threshold of two cardiac cycles plus both a designated time before the two cardiac cycles and a designated time after the two cardiac cycles. The processor 116 may automatically save a third sequence of images (including, for example, both the first sequence of images and the second sequence of images) as a cineloop in the non-volatile memory 120. Thus, even though the ultrasound imaging system 100 was in a retrospective image capture mode, and the store command was received at the time $T_4$, the processor 116 controlled the ultrasound probe 106 to continue acquiring the second sequence of images from the time $T_4$, when the store command was received, to the time $T_6$. By step 616, the processor 116 has saved, as a cineloop, the third sequence of images (including both the first sequence of images and the second sequence of images), which meets or exceeds the length threshold of two cardiac cycles plus both a designated time before the two cardiac cycles and a designated time after the two cardiac cycles. As discussed previously, according to other embodiments, the processor 116 may be configured to select as the third sequence of images, less than all of the images in the first sequence of images and/or less than all of the images in the second sequence of images.

FIG. 8 will also be used to describe an embodiment where the third sequence of images includes less than the combination of the first sequence of images and the second sequence of images. As discussed previously, FIG. 8 shows a first time period $P_1$ and a second time period $P_2$. According to an exemplary embodiment, the threshold length may be 2 cardiac cycles. According to an embodiment, the first sequence of images acquired during the first time period $P_1$ and the second sequence of images acquired during the second time period $P_2$ may be stored in the volatile memory 119. However, the length threshold may be 2 cardiac cycles. According to this exemplary embodiment, the combination of the first sequence of images (acquired during the first time period $P_1$) and the second sequence of images (acquired during the second time period $P_2$) exceeds the threshold length of two cardiac cycles. According to an embodiment, the third sequence of image may meet the length threshold. For example, the third sequence of images may include a portion of the first sequence of images and a portion of the second sequence of images. For example, the third sequence of images (which is saved as a cineloop at step 616) may include a first portion of the first sequence of images acquired from the time $T_2$ to the time $T_4$ and a second portion of the second sequence of images acquired from the time $T_4$ to the time $T_5$. The portion of the first sequence of images from the time $T_1$ to the $T_2$ is not saved in the cineloop and the portion of the second sequence of images from the time $T_5$ to $T_6$ is not saved in the cineloop according to an embodiment. The third sequence of images includes images that were consecutively acquired from the time $T_2$ to the time $T_5$ according to an example. According to an exemplary embodiment, the third sequence of images stored as the cineloop in the non-volatile memory 120 may meet the length threshold of two cardiac cycles.

Still referring to FIG. 8, according to other embodiments, the third sequence of images may include all of the first sequence of images (acquired during the first time period $P_1$) and only a portion of the second sequence of images (acquired during the second time period $P_2$). For example, the third sequence of images (stored as a cineloop) may include the portion of the second sequence of images acquired from $T_4$ to $T_5$, but not the portion acquired from time $T_5$ to $T_6$. According to other embodiments, the third sequence of image may include all of the second sequence of images (acquired during the second time period $P_2$) and only a portion of the first sequence of images (acquired during the first time period $P_1$). For example, the third sequence of images (stored as a cineloop) may include the portion of the first sequence of images acquired from $T_2$ to $T_4$, but not the portion acquired from time $T_1$ to $T_2$.

Figure 9:
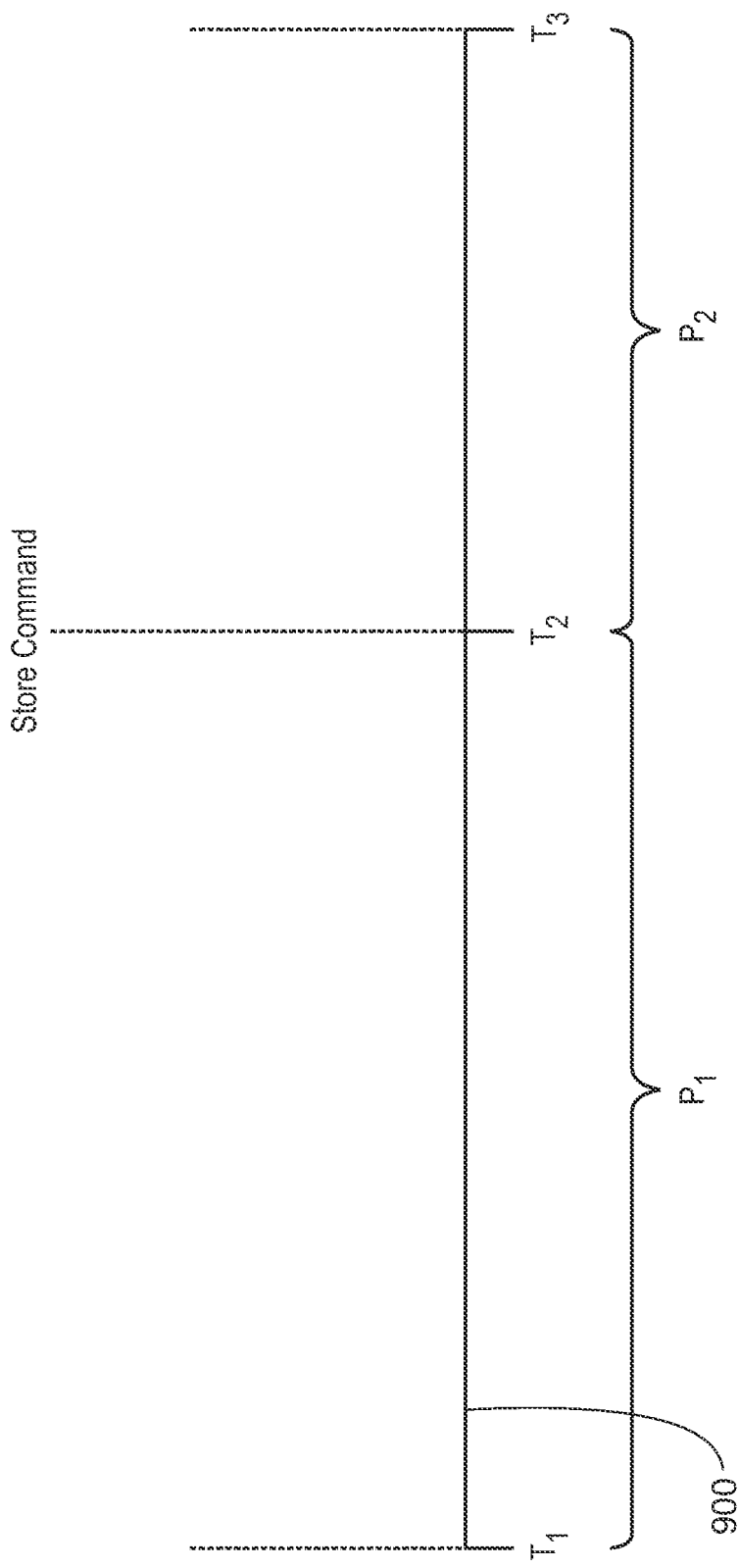
FIG. 9 is a representation of a time line in accordance with an embodiment.

FIG. 9 is a timeline in accordance with an exemplary embodiment. FIG. 9 includes a timeline 900. The timeline 900 illustrates a first time period $P_1$ and a second time period $P_2$. The first time period $P_1$ and the second time period $P_2$ are both shown with respect to the timeline 900. FIG. 9 will be described with respect to the method 600, which was previously described with respect to FIG. 6. At step 602, the clinician initiates a live ultrasound scanning session. According to an embodiment, the first sequence of images are acquired during the first time period $P_1$, which corresponds to the time period from a time $T_1$ to a time $T_2$. The first sequence of images are saved in the volatile memory 119. At step 606, the processor 116 receives a store command at a time $T_2$ while the ultrasound imaging system is in a retrospective image capture mode. At step 608, the processor 116 compares the first sequence of images (i.e., the images acquired during the first time period P1) to the length threshold. The length threshold may be an amount of time. According to an exemplary embodiment that will be discussed with respect to FIG. 9, the amount of time may be 3 seconds, but it should be appreciated that the amount of time may be a different number of seconds, including fractions of a second, according to various embodiments. According to an exemplary embodiment, the first sequence of images, which was acquired during the first time period $P_1$, is less than the length threshold, with is 3 seconds according to an embodiment. Since the first sequence of images is less than the length threshold at step 608, the processor 116 automatically continues to acquires a second sequence of images at the time $T_2$. As discussed previously with respect to FIG. 6, there is no gap or lag between the end of the first sequence of images and the start of the second sequence of images. On the example shown in FIG. 9, the processor 116 controls the ultrasound probe 116 to continue acquiring the second sequence of images until the combination of the first sequence of images (acquired during the first time period $P_1$) and the second sequence of images (acquired during a second time period $P_2$) meets or exceeds the length threshold, which is 3 seconds according to an exemplary embodiment. According to an embodiment, the length threshold may be an amount of time. On FIG. 9, the combination of the first time period $P_1$ and the second time period $P_2$ meets or exceeds the length threshold of 3 seconds. The time from $T_1$ to $T_3$ is equal to the amount of time. Therefore, the processor 116 controls the ultrasound probe 106 to continue acquiring the second sequence of images until the sum of the first sequence of images and the second sequence of images meets or exceeds the length threshold, which is an amount of time according to an exemplary embodiment.

The processor 116 may automatically save a third sequence of images, which may include both the first sequence of images (acquired from time $T_1$ to time $T_2$) and the second sequence of images (acquired from time $T_2$ to time $T_3$), as a cineloop in the non-volatile memory 120. Thus, even though the ultrasound imaging system 100 was in a retrospective image capture mode, and the store command was received at the time $T_2$, the processor 116 controlled the ultrasound probe 106 to continue acquiring the second sequence of images from the time $T_2$ to the time $T_3$. By step 616, the processor 116 has saved, as a cineloop the third sequence of images (including the first sequence of images and the second sequence of images, according to an embodiment) which meets or exceeds the length threshold. As discussed previously, according to other embodiments, the processor 116 may be configured to select as the third sequence of images, less than all of the images in the first sequence of images and/or less than all of the images in the second sequence of images.

Figure 10:
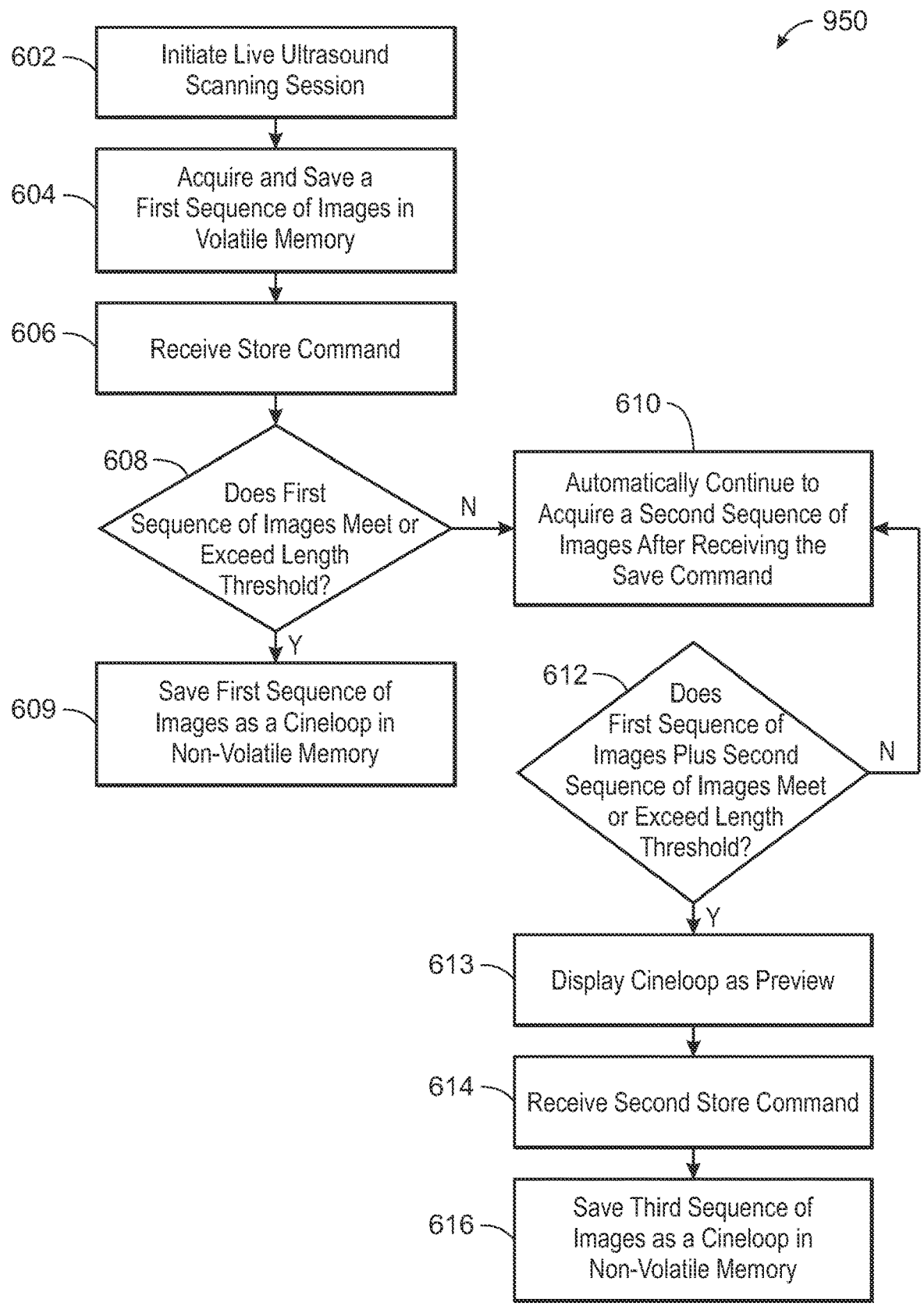
FIG. 10 is a flow chart of a method in accordance with an embodiment.

FIG. 10 is a flow chart of a method 950 in accordance with an exemplary embodiment. The individual blocks of the flow chart represent steps that may be performed in accordance with the method 950. Additional embodiments may perform the steps shown in a different sequence and/or additional embodiments may include additional steps not shown in FIG. 10. The technical effect of the method 950 is the storage of a third sequence of images in the non-volatile memory 120, where the third sequence of images meets or exceeds a length threshold. The method 950 may be performed with the ultrasound imaging system 100 shown in FIG. 1. The method 950 will be described in detail hereinafter.

The method 950 includes many of the same steps that were previously described with respect to the method 600. These steps are identified with the same reference number as those that were previously described with respect to the method 600. Steps 602, 604, 606, 608, 609, 610, and 612 were previously described with respect to the method 600 and will not be described in detail again with respect to the method 950.

At step 612, if the first sequence of images plus the second sequence of images meets or exceeds the length threshold, then the method 950 advances to step 613. At step 613, the processor 116 display the cineloop as a preview on the display device 118. According to an exemplary embodiment, this may entail displaying both the first sequence of images plus the second sequence of images as a repeating loop (i.e., a cineloop) on the display device 118. Displaying the cineloop as a preview at step 613 enables the clinician to preview the cineloop. Previewing the cineloop at step 613 allows the clinician to make sure he/she is satisfied with the cineloop prior to committing the cineloop to the non-volatile memory 120. The clinician may review the cineloop for quality while the cineloop is being displayed at step 613. This may include one or more of the following: checking to see that the correct anatomy is featured in the first and second sequences of images; checking to ensure that the first and second sequences of images do not include any major image artifacts; checking to ensure that the first and second sequences of images do not include any abnormal beats; or checking for any other quality parameters.

After previewing the cineloop at step 613, and assuming that the clinician wants to save the cineloop to the non-volatile memory 120, at step 614, the processor 116 receives a second store command based on an input through the user interface 115. According to an exemplary embodiment, receiving the second store command may include receiving a control signal due to the activation of the store button 142. The second store command may be input using a different control according to various embodiments.

After receiving the second store command, at step 616, the processor 116 saves a third sequence of images, including both the first sequence of images and the second sequence of images, as a cineloop in the non-volatile memory 120. As discussed previously, according to other embodiments, the processor 116 may be configured to select as the third sequence of images, less than all of the images in the first sequence of images and/or less than all of the images in the second sequence of images.

The technique of the method 950 is advantageous because it ensures, even while in a retrospective image capture mode that the cineloop stored in the non-volatile memory 120 meets or exceeds the length threshold. This, in turn, ensures that the cineloop is long enough to be used with any analysis and measurement tools, such as cardiac analysis and measurement tools. The method 950 also displays the first and second sequences of images as a cineloop prior to saving the third sequence of images (including both the first sequence of images and the second sequence of images) as the cineloop in the non-volatile memory 120. This allows the clinicians to confirm the image quality of the first sequence of images and the second sequence of images prior to saving the third sequence of images as the cineloop in the non-volatile memory 120. Furthermore, the method 950 reduces or eliminates the risk that the clinician will need to perform an additional acquisition, as part of either the same or a different scanning session, in order to successfully store a cineloop that meets or exceeds the length threshold. According to conventional methods, it is oftentimes necessary to perform multiple acquisitions and/or different scanning sessions in order to save a sequence of images that meets or exceeds the length threshold. If another acquisition and/or scanning session is required, then it is oftentimes necessary for the clinician to reposition and/or reorient the ultrasound probe 106 before performing the additional acquisition/scanning session. Repositioning the ultrasound probe 106 takes additional time, which is burdensome to both the patient and the clinician. The method 950 therefore saves time for both the patient and the clinician by reducing or eliminating the need to perform additional acquisitions to acquire store cineloops that are long enough for the analysis and measurement tools.

According to an embodiment, a method of ultrasound imaging includes initiating a live ultrasound scanning session. The method includes acquiring and saving a first sequence of images in a volatile memory during the live ultrasound scanning session. The method includes receiving a store command while in a retrospective image capture mode during the live ultrasound scanning session. The method includes detecting, with a processor, that the first sequence of images does not meet a length threshold and, in response to detecting that the first sequences of images does not meet the length threshold, automatically continuing to acquire a second sequence of images after receiving the store command. The method includes detecting, with the processor, that the combination of the first sequence of images and the second sequence of images meets or exceeds the length threshold. The method includes saving a third sequence of images as a cineloop in a non-volatile memory, wherein the third sequence of images includes both at least a portion of the first sequence of images and at least a portion of the second sequence of images, and wherein the third sequence of images meets or exceeds the length threshold.

According to an embodiment, the method also includes retrieving the cineloop from the non-volatile memory and displaying the cineloop on a display device.

According to an embodiment, saving the third sequence of images as the cineloop in the non-volatile memory is performed automatically by the processor in response to said detecting that the combination of the first sequence of images and the second sequence of images meets or exceeds the length threshold.

According to an embodiment, the length threshold includes one of: a specified number of cardiac cycles; the specified number of cardiac cycles plus a first designated amount of time before the specified number of cardiac cycles; the specified number of cardiac cycles plus a second designated amount of time after the specified number of cardiac cycles, or the specified number of cardiac cycles plus both the first designated amount of time before the specified number of cardiac cycles and the second designated amount of time after the specified number of cardiac cycles.

According to an embodiment, the specified number of cardiac cycles is one cardiac cycle.

According to an embodiment, the specified number of cardiac cycles two cardiac cycles.

According to an embodiment, the length threshold comprises an amount of time.

According to an embodiment, the method further comprises displaying both the first sequence of images and the second sequences of images as the cineloop on a display device prior to said saving the third sequence of images as the cineloop in a non-volatile memory.

According to an embodiment, saving the third sequence of images as the cineloop in the non-volatile memory is performed in response to receiving a second store command.

According to an embodiment, the method further includes calculating a metric based on the cineloop saved in the non-volatile memory and displaying the metric on a display device.

According to an embodiment, an ultrasound imaging system includes an ultrasound probe, a user interface, a volatile memory, a non-volatile memory, a display device, and a processor. The processor is configured to receive an initiation of a live ultrasound scanning session. The processor is configured to control the ultrasound probe to acquire a first sequence of images. The processor is configured to save the first sequence of images in the volatile memory during the live scanning session. The processor is configured to receive a store command via the user interface while in a retrospective image capture mode during the live ultrasound scanning session. The processor is configured to detect that the first sequence of images does not meet a length threshold and, in respond to detecting that the first sequence of images does not meet the length threshold, automatically control the ultrasound probe to continue to acquire a second sequence of images after receiving the store command. The processor is configured to detect that the combination of the first sequence of images and the second sequence of images meets or exceeds the length threshold. The processor is configured to save a third sequence of images as a cineloop in the non-volatile memory, wherein the third sequence of images includes both at least a portion of the first sequence of images and at least a portion of the second sequence of images, and wherein the third sequence of images meets or exceeds the length threshold.

According to an embodiment, the processor is also configured to retrieve the cineloop from the non-volatile memory and display the cineloop on the display device According to an embodiment, the processor is also configured to automatically save the third sequence of images as the cineloop in the non-volatile memory in respond to detecting that the combination of the first sequence of images and the second sequence of images meets or exceeds the length threshold.

According to an embodiment, the length threshold comprises one of: a specified number of cardiac cycles; the specified number of cardiac cycles plus a first designated amount of time before the specified number of cardiac cycles; the specified number of cardiac cycles plus a second designated amount of time after the specified number of cardiac cycles, or the specified number of cardiac cycles plus both the first designated amount of time before the specified number of cardiac cycles and the second designated amount of time after the specified number of cardiac cycles.

According to an embodiment, the specified number of cardiac cycles is one cardiac cycle.

According to an embodiment, the specified number of cardiac cycles two cardiac cycles.

According to an embodiment, the length threshold comprises an amount of time.

According to an embodiment, the processor is configured to display both the first sequence of images and the second sequence of images on the display device prior to saving the third sequence of images as the cineloop in the non-volatile memory.

According to an embodiment, the processor is configured to save the third sequence of images as the cineloop in the non-volatile memory in response to receiving a second store command.

According to an embodiment, the processor is further configured to calculate a metric based on the cineloop saved in the non-volatile memory and display the metric on the display device.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of ultrasound imaging comprising:
   initiating a live ultrasound scanning session;
   acquiring and saving a first sequence of images in a volatile memory during the live ultrasound scanning session;
   receiving a store command while in a retrospective image capture mode during the live ultrasound scanning session;
   detecting, with a processor, that the first sequence of images does not meet a length threshold and, in response to said detecting that the first sequence of images does not meet the length threshold, automatically continuing to acquire a second sequence of images after said receiving the store command;

detecting, with the processor, that the combination of the first sequence of images and the second sequence of images meets or exceeds the length threshold; and saving a third sequence of images as a cineloop in a non-volatile memory, wherein the third sequence of images includes both at least a portion of the first sequence of images and at least a portion of the second sequence of images, and wherein the third sequence of images meets or exceeds the length threshold.

2. The method of claim 1, further comprising retrieving the cineloop from the non-volatile memory and displaying the cineloop on a display device.

3. The method of claim 1, wherein said saving the third sequence of images as the cineloop in the non-volatile memory is performed automatically by the processor in response to said detecting that the combination of the first sequence of images and the second sequence of images meets or exceeds the length threshold.

4. The method of claim 1, wherein the length threshold comprises one of: a specified number of cardiac cycles; the specified number of cardiac cycles plus a first designated amount of time before the specified number of cardiac cycles; the specified number of cardiac cycles plus a second designated amount of time after the specified number of cardiac cycles, or the specified number of cardiac cycles plus both the first designated amount of time before the specified number of cardiac cycles and the second designated amount of time after the specified number of cardiac cycles.

5. The method of claim 4, wherein the specified number of cardiac cycles is one cardiac cycle.

6. The method of claim 4, wherein the specified number of cardiac cycles is two cardiac cycles.

7. The method of claim 1, wherein the length threshold comprises an amount of time.

8. The method of claim 1, wherein the method further comprises displaying both the first sequence of images and the second sequences of images as the cineloop on a display device prior to said saving the third sequence of images as the cineloop in the non-volatile memory.

9. The method of claim 8, wherein said saving the third sequence of images as the cineloop in the non-volatile memory is performed in response to receiving a second store command.

10. The method of claim 1, wherein the method further comprises calculating a metric based on the cineloop saved in the non-volatile memory and displaying the metric on a display device.

11. An ultrasound imaging system comprising:
an ultrasound probe;
a user interface;
a volatile memory;
a non-volatile memory;
a display device; and
a processor, wherein the processor is configured to:
receive an initiation of a live ultrasound scanning session;
control the ultrasound probe to acquire a first sequence of images;
save the first sequence of images in the volatile memory during the live ultrasound scanning session;

receive a store command via the user interface while in a retrospective image capture mode during the live ultrasound scanning session;
detect that the first sequence of images does not meet a length threshold and, in respond to detecting that the first sequence of images does not meet the length threshold, automatically control the ultrasound probe to continue to acquire a second sequence of images after receiving the store command;
detect that the combination of the first sequence of images and the second sequence of images meets or exceeds the length threshold; and
save a third sequence of images as a cineloop in the non-volatile memory, wherein the third sequence of images includes both at least a portion of the first sequence of images and at least a portion of the second sequence of images, and wherein the third sequence of images meets or exceeds the length threshold.

12. The ultrasound imaging system of claim 11, wherein the processor is further configured to retrieve the cineloop from the non-volatile memory and display the cineloop on the display device.

13. The ultrasound imaging system of claim 11, wherein the processor is configured to automatically save the third sequence of images as the cineloop in the non-volatile memory in response to detecting that the combination of the first sequence of images and the second sequence of images meets or exceeds the length threshold.

14. The ultrasound imaging system of claim 11, wherein the length threshold comprises one of: a specified number of cardiac cycles; the specified number of cardiac cycles plus a first designated amount of time before the specified number of cardiac cycles; the specified number of cardiac cycles plus a second designated amount of time after the specified number of cardiac cycles, or the specified number of cardiac cycles plus both the first designated amount of time before the specified number of cardiac cycles and the second designated amount of time after the specified number of cardiac cycles.

15. The ultrasound imaging system of claim 14, wherein the specified number of cardiac cycles is one cardiac cycle.

16. The ultrasound imaging system of claim 14, wherein the specified number of cardiac cycles two cardiac cycles.

17. The ultrasound imaging system of claim 11, wherein the length threshold comprises an amount of time.

18. The ultrasound imaging system of claim 11, wherein the processor is configured to display both the first sequence of images and the second sequence of images on the display device prior to saving the third sequence of images as the cineloop in the non-volatile memory.

19. The ultrasound imaging system of claim 11, wherein the processor is configured to save the third sequence of images as the cineloop in the non-volatile memory in response to receiving a second store command.

20. The ultrasound imaging system of claim 11, wherein the processor is further configured to:
calculate a metric based on the cineloop saved in the non-volatile memory; and
display the metric on the display device.

* * * * *